(12) United States Patent
Class

(10) Patent No.: US 9,415,089 B2
(45) Date of Patent: *Aug. 16, 2016

(54) METHODS OF TREATING VIRALLY-INFECTED LIVING CELLS WITH HISTONES

(71) Applicant: Symbiotic Genellschaft zur Erforschung auf dem Geibeit der Biotechnologie, MBH, Saarbrucken (DE)

(72) Inventor: Reiner Class, Saarlouis (DE)

(73) Assignee: Symbiotic Genellschaft zur Erforschung auf dem Geibeit der Biotechnologie, MBH, Saarbrucken (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/074,585

(22) Filed: Nov. 7, 2013

(65) Prior Publication Data

US 2014/0066366 A1 Mar. 6, 2014

Related U.S. Application Data

(63) Continuation of application No. 13/436,788, filed on Mar. 30, 2012, now abandoned, which is a continuation of application No. 11/594,983, filed on Nov. 9, 2006, now abandoned.

(51) Int. Cl.
*A61K 38/17* (2006.01)
*A61K 45/06* (2006.01)

(52) U.S. Cl.
CPC ............. *A61K 38/1709* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,818,763 | A | 4/1989 | Rusch et al. |
| 5,182,257 | A | 1/1993 | Zeppezauer et al. |
| 2001/0046976 | A1 | 11/2001 | Class et al. |
| 2003/0017987 | A1* | 1/2003 | Zeppezauer et al. ............ 514/12 |
| 2003/0078204 | A1 | 4/2003 | Pohlmeyer et al. |

FOREIGN PATENT DOCUMENTS

| | | |
|---|---|---|
| EP | 0392315 B1 | 9/1994 |
| EP | 1370248 B1 | 9/2010 |
| WO | 98/46252 A1 | 10/1998 |
| WO | 01/38522 A1 | 5/2001 |

OTHER PUBLICATIONS

Albig et al., Gene, 1997, 184:141-148.*
Kennedy et al., PNAS, Nov. 25, 2003, 100(24):14269-14274.*
Doenecke, eLS, 2014, pp. 1-11.*
Class et al., "#4803 Formation of a Lethal Membrane Complex Caused by Selective Binding of Histone H1 to Leukemia Cells Membranes", Proceedings of the American Association for Cancer Research Annual Meeting, 91st Annual Meeting of the American Association for Cancer Research. San Francisco, California, USA, Apr. 1-5, 2000, vol. 41, Mar. 2000, pp. 755-756.
Class et al., Characterization of a Novel Membrane-Protein Found in Leukemia Cells That Causes Rapid Cell Death Upon Binding to Histone H1, Proceedings of the Annual Meeting of The American Association for Cancer Research, vol. 38, Mar. 1997, p. 231, abstract.
Class et al., Histone H1 Suppresses Tumor Growth of Leukemia Cells In Vitro, Ex Vivo and in an Animal Model Suggesting Extracellular Functions of Histones, American Journal of Clinical Oncology, 1996, 19(5):522-531.
Class et al., Leukemia-Derived Cell Lines Display Surface Protein Ligand for Histone HI. Histone HI Suppresses Tumor Growth of Leukemia Cells In Vitro, Ex Vivo and in an Animal Model Suggesting Extracellular Functions of Histones, Cellular and Molecular Biology, 1996, 42: S25-S26, Abstract.
Grow Ann et al., New Biochip Technology for Label-Free Detection of Pathogens and their Toxins. Journal of Microbiological Methods, vol. 53, No. 2, May 2003, pp. 221-233, abstract.
Happel et al., Gene, 431:1-12 (2009).
IPRP, PCT/EP05/003257, Jun. 13, 2007.
ISR, PCT/EP05/003257, May 27, 2005.
Izzo et al., Biol. Chern., 389:333-343 (2008).
Marquette et al., "Design of Luminescent Biochips Based on Enzyme, Antibody, or DNA Composite Layers", Analytical and Bioanalyticai Chemistry, vol. 377, No. 5, Nov. 2003, pp. 922-928, abstract.
Pohlmeyer et al., The Recombinant Human Histones H1 Zero and H1.2 Cause Different Toxicity Profiles on the Human Leukemia Cell Line K562, Anticancer Research, Helenic Anticancer Institute, Athens, GR, vol. 20, No. 4, Jul. 2000, pp. 2499-2503, abstract.
Puebla al., Journal of Biotechnology, 2003, 105:215-226.
Pyo al., Protein Expression and Purification, 2001 23: 38-44.
Sancho et al., PLoS Genetics, 4(10):1-17, abstract (2008).
Tamura et al., "Inhibition of Attachment of Virions of Norwalk Virus to Mammalian Cells by Soluble Histone Molecules." Archives of Virology, vol. 148, No. 9, Sep. 2003, abstract.
Vani et al., Histone H1 Modulates Immune Status in Experimental Breast Cancer, Chemotherapy, S. Karger, Basel, CH, vol. 49, No. 5, Sep. 2003, pp. 252-256, abstract.

* cited by examiner

*Primary Examiner* — Nicole Kinsey White
(74) *Attorney, Agent, or Firm* — One3 IP Management, P.C.; Annette S. Parent; Dean G. Stathakis

(57) ABSTRACT

There is provided a biologically-active agent, in particular, for the early diagnosis and/or preventative therapy of virally-infected living cells, the efficacy of which is selective for the cell membranes of the virally-infected cells, which are modified after viral infection. The agent includes at least one component, selected from a group of materials, including recombinant human histone H1 or at least an H1 subtype or the active portion thereof. The appropriate biological activity for killing a virally-infected cell at the modified cell membrane thereof through cooperation with similarly or differently active agent components may be achieved, which together form a biologically-effective complex with increased biological activity.

18 Claims, 2 Drawing Sheets

METHODS OF TREATING VIRALLY-INFECTED LIVING CELLS WITH HISTONES

CROSS-REFERENCES TO RELATED APPLICATIONS

This application is a continuation of U.S. patent application Ser. No. 13/436,788, filed Mar. 30, 2012, which is a continuation of U.S. patent application Ser. No. 11/594,983, filed Nov. 9, 2006, now abandoned, which claims priority to International Application No. PCT/EP2005/003257, filed Mar. 29, 2005, which claims priority to European Patent Application No. 04011015.7, filed May 7, 2004, all of which are incorporated herein by reference in their entirety for all purposes.

BACKGROUND OF THE INVENTION

Viruses can cause a large number of different diseases. One can discriminate two basic classes of viruses: DNA and RNA viruses. The group of DNA viruses contains, for example, the family of herpes viruses like the Epstein-Barr-Virus (ERV) and the smallpox virus (also known as variola). The class of RNA viruses contains the family of human retroviruses HIV (human immunodeficiency virus) or the measles and influenza viruses. Members of both classes represent major health risks for humankind. In contrast to bacterial infections, which usually can easily been treated with antibiotics, no specific and successful treatment regimen exists for most viral infections. In most cases, the early verification of the presence of a viral infection is extremely difficult and usually only recognizable indirectly through the detection of a specific anti-viral immune response. However, latter one takes about a week to become measurable. The immune system is mostly turned adrift due to the fact that no effective treatment options exist as it is exemplified in the case of ERV, a viral infection that can cause infectious mononucleosis (Pfeiffer glandular fever). Additionally, the function of the immune system can only be supported by using established medication.

BRIEF SUMMARY OF THE INVENTION

In one aspect, the invention provides a biologically active agent particularly with regard to an early diagnosis and/or preventive therapy of living, virus-infected cells whereas its biological activity is selectively directed against the cell membrane of said virus-infected cell, which has been, after becoming infected with the virus, modified in a characteristic way whereas the biological agent contains at least one component or is made up of one component selected from the group of substances consisting of histone proteins, covalently modified histone proteins, histone-like polypeptides and histone-like peptides.

In another aspect, the invention provides a biochip for the diagnosis of virus-infected cells whereas a selected number of different biologically active agents with one particular biological activity each is deposited on the surface of said biochip. The latter one serves as a tool for the determination of an individual profile for a particular disease whereas the agents will be selected from the group consisting of histone proteins, covalently modified histone proteins, histone-like polypeptides and biologically active components of histones and histone-like peptides.

DETAILED DESCRIPTION OF THE INVENTION

Figure 1:
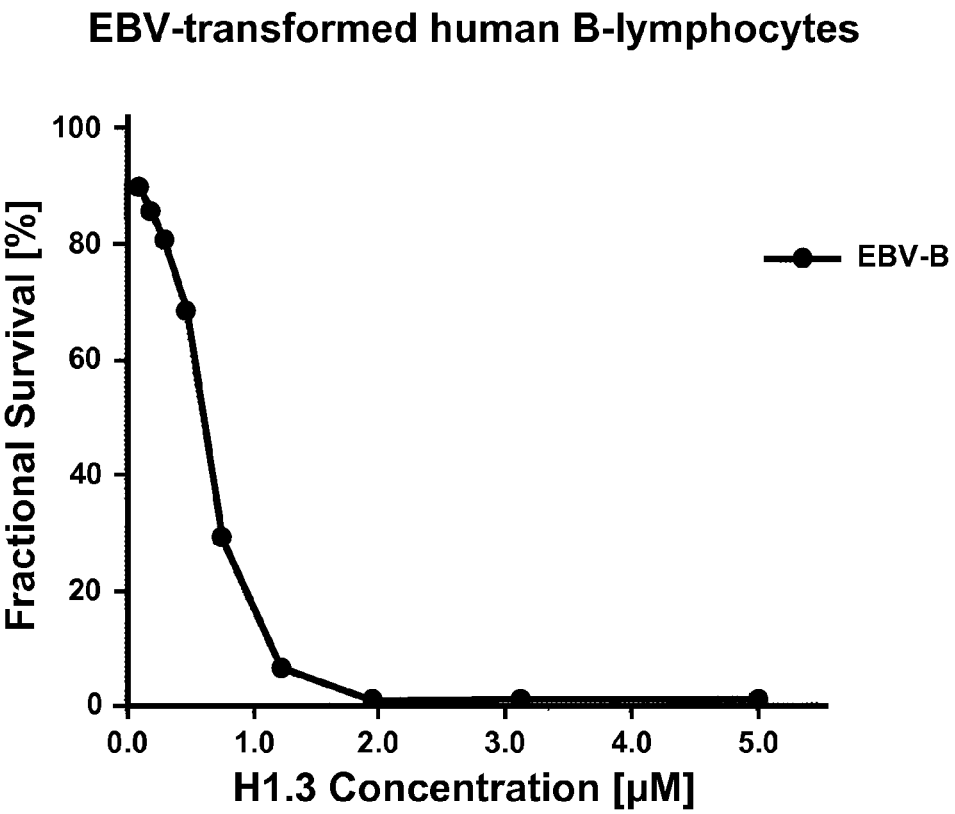
FIG. 1: Fractional survival rate of Epstein-Barr-Virus (EBV)-infected human B-lymphocytes after incubation with recombinant human histone H1.3 (rhH1.3) versus the historic concentration shown in micromolar.

The invention is entrusted with the task to present a biologically active agent that is capable of selectively diagnosing and eliminating virus-infected cells already as early as immediately after the initial infection occurred and prior to the development of a recognizable immune response against the virus and the onset of the viral replication cycle within the cell. At therapeutic doses of 0.5 to 2 µM (for example), the biologically active agent is, to the greatest extent possible, free of unwanted side effects for the organism and its immune system. In other words, the biologically active agent should be suitable for early diagnosis and/or preventive therapy of living, virus-infected cells, in particular in mammals and humans.

Said task will be accomplished through a biologically active agent containing at least one component selected from the group consisting of histones, covalently modified histones, histone-like polypeptides and biologically active amino acid sequences of histones and histone-like peptides. According to the present invention, it can be an advantage to support or augment the therapeutic efficacy of established antiviral drugs through the addition of said biologically active agent in such a way that the amount of biostatic drugs can be lowered without losing overall therapeutic activity.

The biologically active agent used for diagnostic and therapeutic purposes in human health care contains, in a favorable way, recombinant human histone H1 or at least a histone H1 subtype such as H1.0, H1.1, H1.2, H1.3, H1.4, H1.5, H1.t, H1.x or their biologically active parts.

Furthermore, the agent according to this invention can also contain a selected number of different biologically active histones and/or biologically active parts thereof.

Biological activity in this regards particularly means a stretch of amino acid sequences of said agent with a biological activity against cell membranes of virus-infected cells.

Advantageous variations of the embodiment are revealed by the features of the subclaims. The invention also contains a biochip for the selection of biological agents according to this invention with maximal biological activity against virus-infected cells within the human organism or a mammal. Said biochip factors in the respective properties of the virus-infected cells and thus allows an optimal diagnosis and/or therapy.

On said biochip for the diagnosis, according to this invention, of virus-infected cells, a selected number of different biological agents is placed, each with a biological activity on the biochip serving for the determination of an individual disease profile whereas the biologically active agents are selected from the group of compounds consisting of histones, covalently modified histories, histone-like polypeptides and biologically active amino acid sequences of histones and histone-like peptides. The immobilization of the selected biologically active agents on the matrix of said biochip can be accomplished through PEG-sequences, oligopeptides, oligopeptides with N-terminal cysteine, gold or antibodies.

The invention is based on the observation that the membranes of virus-infected cells become modified in a characteristic way immediately after the infection occurred and still prior to the onset of the viral replication cycle within the cells. Said virus-specific, characteristic modifications of the membranes are recognized by the biologically active agent according to this invention, especially by histone H1 or a biologically active part thereof. These events are independent of the type of virus that infected the cells.

Herewith, according to the present invention, a diagnosis and/or therapy of virus-infected cells within an organism becomes possible already at a point in time at which no disease symptoms can be identified and the immune system has not yet developed a recognizable immune response against the virus.

For the first time, the biologically active agent according to this invention makes a prophylactic diagnosis of potentially virus-infected people possible. Those people have possibly been exposed to a virus and can already be treated, in case of a positive diagnosis, prior to the outbreak of the disease. Furthermore, in absence of an early diagnosis, a preventive therapeutic regimen can already be initiated using the biologically active agent according to this invention even if a virus infection through the considered or potential contact with virus-infected people or animals is only suspected.

The timely therapy described above has the essential advantage that the immune system of the virus-infected person largely remains functional and capable of unfolding a supportive function regarding the therapy with the biologically active agent according to this invention.

The characteristic modifications or alterations at the cellular membrane associated with the viral infection occurring immediately after the infection can be caused by the contact of the virus with the cell membrane or are based on the modifications of the metabolism in the cell after the invasion of the virus. This event can result in modifications of the cell membrane whereas said modifications are recognized by the biologically active agent according to this invention. The presence of a specific binding partner on the cellular surface is not required for the contact between the biologically active agent according to this invention and the cellular membrane. This is further indicative of the fact that the biologically active agent according to this invention damages the cell membrane after binding of said biologically active agent to the cellular membrane in such a way that the virus-infected cell lyses. The activity sufficient to kill a virus-infected cell can also be adjusted in a way that, through the first contact of components of the respective biologically active agent with the modified cell membrane surface, a positive cooperativity with other biologically active agents is initiated or favored, forming together a biologically active complex with even increased biological activity.

Said positive cooperativity, according to the present invention, can further be facilitated and/or accelerated. This can be accomplished in a way that the biologically active agent consists not only of one particular histone and/or its biologically active components but also of a selected number of different histones and/or biologically active parts thereof.

With the biochip according to the present invention, biological activities of histones and histone-like polypeptides and biologically active sequences thereof towards individual, virus-infected cells can be determined, thereby obtaining an individualized activity profile of the respective patients.

The efficacy of exemplified biologically active agents according to the present invention is described by means of experiments described in the following.

Figure 2:
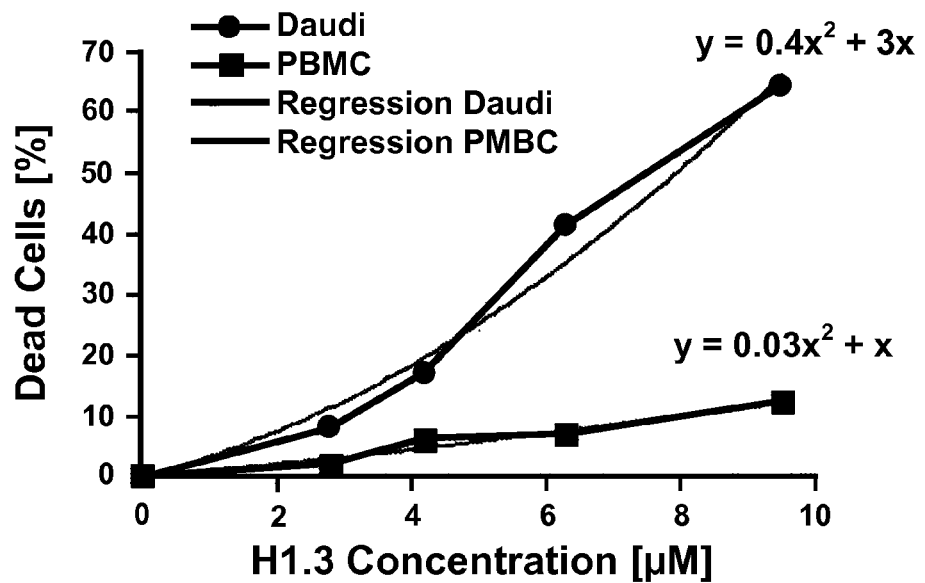
FIG. 2: Killing rate of non-infected peripheral blood mononuclear cells (PBMC) in comparison to Epstein-Barr-Virus nuclear antigen (EBNA)-positive cells of a human Burkitt-lymphoma (Daudi) versus the histone rhH1.3-concentration shown in micromolar and ranging from 0 to 10 µM.
Figure 3:
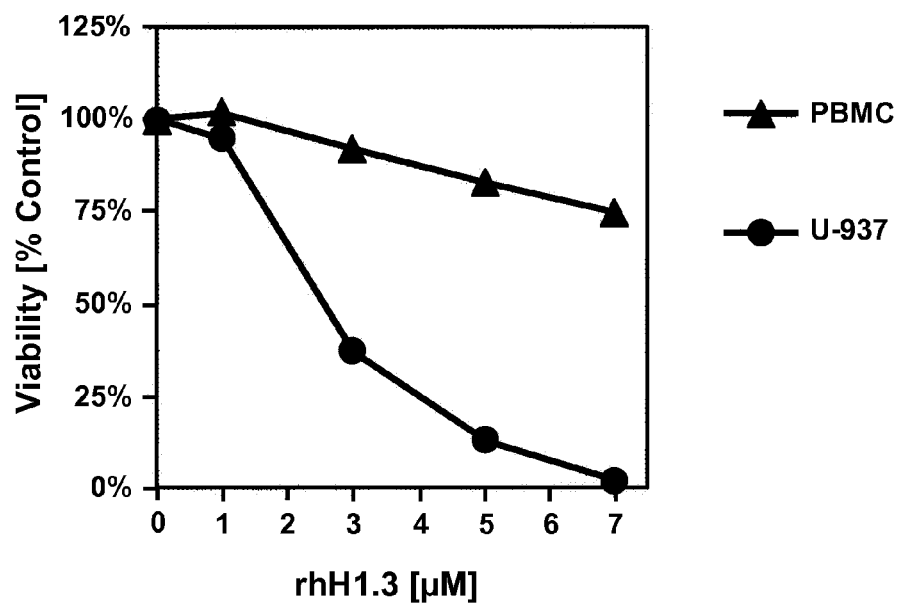
FIG. 3: Fractional survival rate of non-infected peripheral blood mononuclear cells (PBMC) in comparison to cells of a human acute myeloid leukemia (AML) cell line (U-937) versus the historic concentration shown in micromolar and ranging from 0 to 7 µM.

FIGS. 1-3 are proof for the conducted experiments and show that histones can indeed kill virus-infected cells in vitro. in particular, the experiments show:

In FIG. 1, EBV (Epstein-Barr-Virus) infected human B-lymphocytes have been used. After incubation of virus-infected cells in the presence of varying concentrations of rhH1.3 (recombinant human histone H1 subtype 3), a lysis and the respective killing of virus-infected cells can be observed.

FIG. 1 shows the fractional survival rate of Epstein-Barr-Virus (EBV)-infected human B-lymphocytes after incubation with recombinant human histone H1.3 (rhH1.3) versus the histone concentration shown in micromolar.

The amount of histone H1 required to kill said cells is small. Already at a histone H1.3 concentrations as little as 1 $\mu$M, more than 50% of the cells can be lysed. Concentrations above 2 $\mu$M cause complete killing of the virus-infected cells. Thus, the therapeutic range of histone H1.3-concentrations is between 0.5 and 2.0 $\mu$M.

The cell lysis can be explained by the action of histones at the level of the cell membrane, especially the phospholipid bilayer that has been modified by the viral infection. Surprisingly, histones that were originally only found in the nucleus of cells could be identified in the plasma membrane of many cells including, among others, virus-infected cells, It could further be shown that histone H1 binds with high affinity to virus-specific proteins and that histone H1 plays an important role in the viral replication cycle.

The incorporation of foreign proteins such as histories into the cell membrane damages the membrane integrity in a way that soluble proteins, ions and other cell components can exit the cell uncontrollably and subsequently kill the cells.

The incorporation of histones into the cell membrane can be antigen-mediated so that an antigen presented on the cell surface can serve as a binding partner for the histone protein.

After a target cell becomes infected with a virus, it can produce virus-specific as well as cell-specific antigens during the cell cycle which is now under control of the virus. Said antigens can end up on the cell surface where they are presented as antigens. In case of an infection with EBV, EBNA antigens are synthesized. It could be shown in vitro that historic H1 binds those proteins with high affinity.

It is further conceivable that histone binding to the cell membrane occurs without involvement of a classic receptor. The invasion of the virus into the cell could modify the cell membrane in a way that binding of histones to it and the subsequent cell lysis are permissible.

The characteristic dependence of the cell killing from the histone concentration (logarithmically drawn) is indicative of an effect with positive cooperativity. This means that the lytic event is initiated only after a certain threshold concentration of cell-bound histones is reached. After this occurs, the binding of additional historic proteins is facilitated and the cell lysis is accelerated. The same effect can also be expected from homogenous histone solutions of different types, e.g. histone H2, H3 and H4 as well as for heterogeneous historic mixtures.

The lysis of virus-infected cells is highly specific. Non-inflicted cells are either not lysed at all or only slightly incapacitated by histones.

FIGS. 2 and 3 are the negative controls and show the rather mild effects of histone rhH 1.3 towards non-infected lymphocytes, in this case peripheral blood mononuclear cells (PBMC).

FIG. 2 shows the killing rate of non-infected peripheral blood mononuclear cells (PBMC) in comparison to Epstein-Barr-Virus nuclear antigen (EBNA)-positive cells of a human Burkitt-lymphoma (Daudi) versus the histone rhH1.3-concentration shown in micromolar and ranging from 0 to 10 μM.

It can be deduced from the small slope of the curve [$y=0.03x^2+x$] that non-infected peripheral blood mononuclear cells (PBMC) are significantly less affected compared to cells of EBV-infection-generated Burkitt lymphoma cells of the Daudi cell line whose killing rate is characterized by the comparably steep slope of the curve [$y=0.4x^2+3x$].

The curves of FIG. 2 show a parabolic increase of lethality of the virus-infected cells depending on the histone H1.3 concentration. In comparison to the conditions used in EBV-infected B-cells (FIG. 1), killing of non-infected peripheral blood mononuclear cells (PBMC) at high histone H1.3 concentrations of approximately 10 μM is only around 10%. At the same conditions, approximately 70% of Daudi cells are already lysed.

FIG. 3 shows the fractional survival rate of non-infected peripheral blood mononuclear cells (PBMC) in comparison to cells of a human acute myeloid leukemia (AML) cell line (U-937) versus the histone concentration shown in micromolar and ranging from 0 to 7 μM.

The fractional survival rate of the PBMC depicted in FIG. 1 at a histone rhH1.3 concentration of 7 μM is still 75% whereas 100% of the cells of an acute myeloid leukemia (AML) cell line are killed.

Leukemia can be caused by oncogenic viruses such as HTLV-I. In this example, analogous to EBNA-positive Burkitt lymphoma cells (FIG. 2), it becomes evident that the lytic effect of histones is independent from the growth stage of the cell. The cells are recognized and lysed even if they have already changed to lymphoma or leukemia cells through the preceding virus infection.

In contrast, the survival rate of phytohemagglutinin (PHA)-activated normal T-lymphocytes is approximately within the same range as compared to peripheral blood lymphocytes.

Hemagglutinine belongs to the family of glycoproteins of the virus lipid membrane which are responsible for the adhesion of the virus to cell surfaces and thus are considered the most virulent contributing factor of viruses. In cell biology, PHA is often used to stimulate peripheral blood lymphocytes. In the experiments shown here, it becomes evident that the biological activity of histones is not selectively directed against PHA-activated cells.

It can be concluded that the results obtained so far strongly indicated that the selectivity of histone binding is contingent upon the special modification of cell membranes induced, in a specific matter, by the infection of the cell by the virus. Nevertheless, it remains surprising that the histone binding seems to be independent of the virus type and the type of the infected cell and that the effect occurs in members of the DNA-(e.g. EBV) as well as RNA-(e.g. HIV) viruses.

Cells of the immune system such as T- and B-lymphocytes have also been tested. Latter ones rendered susceptible and could be killed using histone H1 after becoming infected with EBV (FIG. 1). A longer lasting infection with EBV can result in the generation of malignant Burkitt lymphomas. The addition of histones to cells in such a malignant stage was also able to induce cell lysis (FIG. 2).

These experiments demonstrated that virus-infected cells are recognized and destroyed by histone H1 independent from the retrograde time of infection. For EBV-infections, the treatment with histone H1 offers an opportunity for a fast diagnosis (e.g. of blood components) and therapy before Burkitt lymphomas or infectious mononucleosis (Pfeiffer glandular fever) can develop. Up to now, early diagnostic tools or effective therapeutic regimens for EBV-infections are still lacking.

Furthermore, the use of histones offers new possibilities for the diagnosis and therapy of virus-induced leukemia.

All proteins have active centers, or areas, respectively, that are required for their specific tasks. Therefore, it is possible to use not only native or recombinantly produced histones for the diagnosis and therapy of virus-infected cells but also modified histones, histone-like polypeptides or active parts thereof. It is important for latter ones that the biologically active centers remain intact. Covalent modifications of histones include phosphorylation, acetylation, ribosylation or ubiquitinytation.

One possibility for the diagnosis of virus-infected cells is represented by a biochip. A biochip is an accumulation of miniaturized assay sites (a.k.a. micro arrays) that have been aligned onto a solid substrate. A biochip allows for simultaneous assays and thus facilitates high throughput testing. A biochip can process thousands of biological reactions in just a few seconds. Using a specially designed optical detection system, positive reactions, i.e. binding sites can be localized.

In our case, different histone types and subtypes, covalently modified histones, histone-like polypeptides or biologically active parts thereof can be attached to a biochip serving as binding anchor for virus-infected cells. Thereby, it becomes possible to evaluate the affinity of different cells of numerous patients to different components of the agent with the goal of determining whether a virus infection is present. The type of binding of the biologically active agents to the biochip surface can be mediated by PEG-sequences, oligopeptides, oligopeptides with terminal cysteine, gold particles or through specific antibodies.

The invention claimed is:

1. A method of treating a viral infection in a mammal suspected of having a viral infection, said method comprising the step of: administering to said mammal a therapeutically effective amount of a biologically active agent comprising a recombinant human histone H1.3 protein prior to diseases symptoms being identified and/or prior to the development of a recognizable immune response against the virus, thereby killing a virus-infected cell and treating said viral infection; wherein said virus-infected cell is a cell infected with a human T-lymphocyte virus type I, a simian immunodeficiency virus, or a human immunodeficiency virus.

2. The method according to claim 1, wherein said mammal is a human.

3. The method according to claim 1, wherein said virus-infected cell is a cell from the immune system.

4. The method according to claim 3, wherein said virus-infected cell is a T-lymphocyte or a B-lymphocyte.

5. The method according to claim 1, wherein said biologically active agent is administered in combination with one or more antiviral drugs.

6. The method according to claim 1, wherein said biologically active agent is administered in combination with a second biologically active agent comprising one or more of a histone H1.0 protein, a histone H1.1 protein, a histone H1.2 protein, a histone H1.4 protein, a histone H1.5 protein, a histone H1.t protein, or a histone H1.x protein.

7. The method according to claim 1, wherein said biologically active agent further comprises one or more of a histone H1.0 protein, a histone H1.1 protein, a histone H1.2 protein, a histone H1.4 protein, a histone H1.5 protein, a histone H1.t protein, or a histone H1.x protein.

8. The method according to claim 1, wherein said viral infection causes a Burkitt's lymphoma or an acute myeloid leukemia.

9. A method of killing a virus-infected cell comprising the step of: contacting said virus-infected cell with a therapeutically effective amount of a histone protein consisting of a recombinant human histone H1.3 protein prior to disease symptoms being identified and/or prior to the development of a recognizable immune response against the virus; wherein said virus-infected cell is a cell infected with an Epstein-Barr virus, a human T-lymphocyte virus type I, a simian immunodeficiency virus, or a human immunodeficiency virus.

10. The method according to claim 9, wherein said virus-infected cell is a cell from the immune system.

11. The method according to claim 9, wherein said virus-infected cell is a T-lymphocyte or a B-lymphocyte.

12. The method according to claim 9, wherein the method further comprises the step of contacting said cell with one or more additional histone proteins selected from of a histone H1.0 protein, a histone H1.1 protein, a histone H1.2 protein, a histone H1.4 protein, a histone H1.5 protein, a histone H1.t protein, or a histone H1.x protein, wherein the contacting with the one or more additional histone proteins occurs after contacting with the recombinant human histone H1.3 protein.

13. The method according to claim 9, wherein said recombinant human histone H1.3 protein is administered at concentration ranging from 0.5 μm to 10 μm.

14. A method of treating a viral infection in a mammal suspected of having a viral infection, said method comprising the step of: administering to said mammal a therapeutically effective amount of a histone protein consisting of a recombinant human histone H1.3 protein prior to disease symptoms being identified and/or prior to the development of a recognizable immune response against the virus; thereby killing a virus-infected cell and treating said viral infection; wherein said virus-infected cell is a cell infected with an Epstein-Barr virus, a human T-lymphocyte virus type I, a simian immunodeficiency virus, or a human immunodeficiency virus.

15. The method according to claim 14, wherein said virus-infected cell is a cell from the immune system.

16. The method according to claim 14, wherein said virus-infected cell is a T-lymphocyte or a B-lymphocyte.

17. The method according to claim 14, wherein said recombinant human histone H1.3 protein is administered at concentration ranging from 0.5 μm to 10 μm.

18. The method according to claim 14, wherein said mammal is a human.

* * * * *